US009682148B2

(12) United States Patent
Hojgaard

(10) Patent No.: US 9,682,148 B2
(45) Date of Patent: Jun. 20, 2017

(54) SOLID ORAL DOSAGE FORM OF TESTOSTERONE DERIVATIVE

(71) Applicant: Solural Pharma APS, Ballerup (DK)

(72) Inventor: Bent Hojgaard, Allerod (DK)

(73) Assignee: Solural Pharma APS, Ballerup (DK)

( * ) Notice: Subject to any disclaimer, the term of this patent is extended or adjusted under 35 U.S.C. 154(b) by 0 days.

(21) Appl. No.: 14/649,687

(22) PCT Filed: Dec. 19, 2013

(86) PCT No.: PCT/EP2013/077300
§ 371 (c)(1),
(2) Date: Jun. 4, 2015

(87) PCT Pub. No.: WO2014/096139
PCT Pub. Date: Jun. 26, 2014

(65) Prior Publication Data
US 2015/0328233 A1  Nov. 19, 2015

(30) Foreign Application Priority Data
Dec. 20, 2012 (EP) .................................... 12198529

(51) Int. Cl.
| | |
|---|---|
| A61K 31/568 | (2006.01) |
| A61K 47/12 | (2006.01) |
| A61K 31/569 | (2006.01) |
| A61K 47/14 | (2017.01) |
| A61K 9/107 | (2006.01) |
| A61K 47/44 | (2017.01) |
| A61K 9/20 | (2006.01) |
| A61K 9/48 | (2006.01) |
| A61K 9/16 | (2006.01) |

(52) U.S. Cl.
CPC ............ *A61K 47/12* (2013.01); *A61K 9/1075* (2013.01); *A61K 9/2009* (2013.01); *A61K 9/2013* (2013.01); *A61K 9/2095* (2013.01); *A61K 9/4858* (2013.01); *A61K 31/568* (2013.01); *A61K 31/569* (2013.01); *A61K 47/14* (2013.01); *A61K 47/44* (2013.01); *A61K 9/1611* (2013.01); *A61K 9/1617* (2013.01)

(58) Field of Classification Search
USPC .......................................... 424/489; 514/178
See application file for complete search history.

(56) References Cited

U.S. PATENT DOCUMENTS

| | | | |
|---|---|---|---|
| 4,098,802 A | 7/1978 | van der Vies | |
| 5,494,914 A | 2/1996 | Labrie | |
| 6,096,338 A | 8/2000 | Lacy | |
| 6,267,985 B1 | 7/2001 | Chen | |
| 6,652,880 B1 * | 11/2003 | Aylwin ................ | A61K 9/1075 424/451 |
| 6,977,083 B1 | 12/2005 | Huebler | |
| 7,138,389 B2 | 11/2006 | Amory | |
| 2004/0122106 A1 * | 6/2004 | Ohta ..................... | A61K 9/0056 514/630 |
| 2004/0127476 A1 | 7/2004 | Kershman | |
| 2005/0100608 A1 | 5/2005 | Ebert | |
| 2005/0176692 A1 | 8/2005 | Amory | |
| 2005/0209345 A1 | 9/2005 | Charman | |
| 2005/0287203 A1 | 12/2005 | Nijs Des | |
| 2008/0305177 A1 | 12/2008 | Kershman | |
| 2008/0317844 A1 | 12/2008 | Dudley | |
| 2009/0075961 A1 | 3/2009 | Ebert | |
| 2010/0136105 A1 | 6/2010 | Chen | |
| 2010/0173882 A1 | 7/2010 | Giliyar | |
| 2011/0039814 A1 | 2/2011 | Huatan | |
| 2011/0251167 A1 | 10/2011 | Dudley | |
| 2012/0322780 A1 | 12/2012 | Giliyar | |

FOREIGN PATENT DOCUMENTS

| | | |
|---|---|---|
| WO | 00/09093 | 2/2000 |
| WO | 0009093 | 2/2000 |
| WO | 00/59482 | 10/2000 |
| WO | 0059482 | 10/2000 |
| WO | 2011/082384 | 7/2011 |
| WO | 2011082384 | 7/2011 |
| WO | 2011129812 | 10/2011 |
| WO | 2012079092 | 6/2012 |

OTHER PUBLICATIONS

Related U.S. Appl. No. 14/135,571 (published as US20140179655), filed Jun. 11, 2011, Interview Summary dated Sep. 18, 2015.
Related U.S. Appl. No. 14/135,571 (published as US20140179655), filed Jun. 11, 2011, Final Office Action dated Jun. 13, 2015.
Related PCT Appln. No. PCT/EP2013/077300 (published as WO2014096139), International Preliminary Report on Patentability, dated Mar. 9, 2015.
Related U.S. Appl. No. 14/135,571 (published as US20140179655), filed Jun. 11, 2011, US Office Action dated Feb. 10, 2015.
Related PCT Appln. No. PCT/EP2013/077300 (published as WO2014096139) response to second written opinion filed Dec. 11, 2014.
Related PCT Appln. No. PCTIEP2013/077300 (published as WO2014096139), 2nd Written Opinion dated Oct. 31, 2014.
Related PCT Appln. No. PCT/EP2013/077300 (published as WO2014096139), Response to 1st Written Opinion dated May 2, 2014.
Related PCT Appln. No. PCT/EP2013/077300 (published as WO2014096139), 1st Written Opinion dated Mar. 21, 2014.
Related PCT Appln. No. PCT/EP2013/077300 (published as WO2014096139), Search Report dated Mar. 21, 2014.
Amory JK et al. Oral testosterone in oil plus dutasteride in men—A pharmacokinetic study. The Journal of Clinical Endocrinology & Metabolism: 90; 2610-2617 (2005).

(Continued)

*Primary Examiner* — Ali Soroush
*Assistant Examiner* — Danielle Sullivan
(74) *Attorney, Agent, or Firm* — Agris & von Natzmer, LLP; Cheryl H. Agris

(57) ABSTRACT

The present invention relates to a pharmaceutical composition comprising a testosterone derivative having a log p of at least 5 and a vehicle, wherein the vehicle comprises a fat component in an amount sufficient to achieve lymphatic absorption in a mammal, wherein the fat component comprises a mono- or triglyceride of long chain fatty acids.

17 Claims, No Drawings

(56) References Cited

OTHER PUBLICATIONS

Amory JK et al. Oral testosterone in oil. Pharmacokinetic effects of 5a reduction by finasteride or dutasteride and food intake in man. Journal of Andrology 27; 72-78 (2006).
Bagchus WM et al. Important effect of food on the bioavailability of oral testosterone undecanoate. Pharmacotherapy 23; 319-325 (2003).
Charman WNA et al. Effects of lipid class and lipid vehicle volume on the intestinal lymphatic transport of DDT. International Journal of Pharmaceutics 33; 165-172 (1986).
Charman WNA et al. Estimating the maximal potential for intestinal lymphatic transport of lipophilic drug molecules. International Journal of Pharmaceutics 34; 175-178 (1986).
Frey H et al. Bioavailability of oral testosterone in males. Eur. Clin. Pharmacol. 16; 345-349 (1979).
Geere G et al. Plasma androgens after a single oral dose of testosterone undecanoate. Archives of Disease in Childhood 55; 218-220 (1980).
Gooren LJG. A Ten-Year Safety Study of the Oral Androgen Testosterone Undecanoate. Journal of Andrology: 15; 212-215; (1994).
Hirschhäuser C et al. Testosterone undecanoate. A new orally active androgen. Acta Endocrinologica 80; 179-187 (1975).
Horst HJ et al. Lymphatic absorption and metabolism of orally administered testosterone undecanoate in man. Klinische Wocher schrift 54; 875-879 (1976).
Houwing NS et al. Pharmacokinetic study in women of three different doses of a new formulation of oral testosterone undecanoate, Andriol Testocaps. Pharmacotherapy 23; 1257-1265 (2003).
Khoo S-M et al. Intestinal lymphatic transport of halofantrine occurs after oral administration of a unit-dose lipid-based formulation to fasted dogs. Pharmaceutical Research 20; 1460-65 (2003).
Malcolmson C et al. A comparison of the incorporation of model steroids into non-ionic micellar and microemulsion systems. J. Pharm. Pharmacol. 45; 141-143 (1993).
Muchow M et al. Production and characterization of testosterone undecanoate-loaded NLC for oral bioavailability enhancement. Drug Development and Industrial Pharmacy 37; 8-14 (2011).
Noguchi T et al. The effect of drug lipophilicity and lipid vehicles on the lymphatic absorption of various testosterone esters. International Journal of Pharmaceutics 24; 173-184 (1985).
Page ST et. al. Nanomilled oral testosterone plus dutasteride effectively normalizes serum testosterone in normal men with induced hypogonadism. Journal of Andrology 29; 222-227 (2008).
Porter CJH et al. Intestinal lymphatic drug transport: an update. Advanced Drug Delivery Reviews 50; 61-80 (2001).
Porter CJH et al. Lipids and lipid-based formulations: optimizing the oral delivery of lipophilic drugs. Nature Reviews 6; 231-248 (2007).
Schnabel PG et al. The effect of food composition on serum testosterone levels after oral administration of Andriol Testocaps. Clinical Endocrinology 66; 579-585 (2007).
Shackleford DM et al. Contribution of lymphatically transported testosterone undecanoate to the systemic exposure of testosterone after oral administration of two andriol formulations in conscious lymph duct-cannulated dogs. The Journal of Pharmacology and Experimental Therapeutics 306; 935-933 (2003).
Shackleford DM et al. Lymphatic Absorption of Orally Administered Prodrugs. In Book: Prodrugs, Challenges and Rewards Part 1 and Part 2: 2.5.7; 653-682 (2007).
Srinivas-Shankar U et al. Review: Testosterone Treatment in Elderly Men. Adv. Ther. 26;25-39 (2009).
Trevaskis NL et al. Lipid-based delivery systems and intestinal lymphatic drug transport—a mechanistic update. Advanced Drug Delivery Reviews 60; 702-716; (2008).
Tso P et al. Randomized structured triglycerides increase lymphatic absorption of tocopherol and retinol compared with the equivalent physical mixture in a rat model of fat malabsorption. The Journal of Nutrition 131; 2157-2163 (2001).
White KL et al. Lymphatic transport of methylnortestosterone undecanoate (MU) and the bioavailability of methylnortestosterone are highly sensitive to the mass of coadministered lipid after oral administration of MU. Journal of Pharmacology and Experimental Therapeutics 331; 700-709 (2009).
Yin AY et al. Reexamination of pharmacokinetics of oral testosterone undecanoate in hypogonadal men with a new self-emulsifying formulation. Journal of Andrology 33; 190-201 (2012).
Yin A et al. Dietary fat modulates the testosterone pharmacokinetics of a new self-emulsifying formulation of oral testosterone undecanoate in hypogonadal men. Journal of Andrology 33; 1282-1290 (2012).
Related EP appln. No. 13819021.0, (national phase application of PCT/EP2013/077300), communication dated Jul. 21, 2016.
Related U.S. Appl. No. 14/135,571 (published as US20140179655), filed Jun. 11, 2011, Interview Summary dated Jul. 12, 2016.
Related U.S. Appl. No. 14/135,571 (published as US20140179655), filed Jun. 11, 2011, Office Action dated Feb. 12, 2016.
Related EP appln. No. 13819021.0, (national phase application of PCT/EP2013/077300), amended claims submitted Jan. 18, 2016.

\* cited by examiner

SOLID ORAL DOSAGE FORM OF TESTOSTERONE DERIVATIVE

CROSS-REFERENCE TO RELATED APPLICATIONS

This is the United States National Phase of PCT Application No. PCT/EP2013/077300 filed 19 Dec. 2013 which claims priority to European Patent Application No. 12198529.5 filed 20 Dec. 2012, each of which are incorporated herein by reference This application relates to U.S. patent application Ser. No. 14/135,571 filed 19 Dec. 2013.

BACKGROUND OF THE INVENTION

Field of the Invention

This invention relates to a pharmaceutical composition comprising a testosterone derivative (such as testosterone undecanoate) having a log P of at least 5 and a vehicle, and this is intended for oral use. Typically, the oral dosage form is a solid dosage form that has a high oral bioavailability of testosterone and at the same time a low variability in absorption compared to prior oral formulations of testosterone and is being delivered via the lymphatic transport system. The oral dosage, such as solid dosage form, further has the advantage of having a reduced or an absence of food effect and it can therefore be taken in both fed and fasted state. This invention also relates to the preparation and composition of a stable solid oral dosage form and methods of use thereof, for instance in treatment of conditions associated with a deficiency or absence of endogenous testosterone in a mammal in need thereof. Typically the composition is administered orally as a testosterone replacement therapy.

Background of the Invention

Testosterone and derivatives thereof, such as Testosterone Undecanoate and Methyltestosterone are indicated as replacement therapy in conditions associated with a deficiency or absence of endogenous testosterone. These products come in a variety of formulations including: gels, patches, injections and oral capsules.

Testosterone is a poorly water-soluble compound. When administered orally Testosterone undergoes extensive first pass metabolism both during absorption in the GI tract and in the liver. Testosterone given orally is known to be mostly deactivated by the liver and intestinal cell lining before reaching circulation. Derivatives of testosterone such as Testosterone Undecanoate and Methyltestosterone have therefore been developed and marketed for oral delivery. Methyltestosterone is a prodrug of testosterone and has a close structural similarity with testosterone but has a methyl group at C17 (17-α derivative) in order to increase oral bioavailability. Methyltestosterone is marketed as Android®, Testered® and Virilon® but is associated with liver toxicity limiting its use. Testosterone Undecanoate (TU) is a lipophillic ester product of Testosterone. Testosterone undecanoate, is non hepatoxic in contrast to 17-α derivative and is marketed as Andriol® or Andriol® Testocaps™ in many countries for oral administration. Testosterone undecanoate is formulated in Castor oil/Propylene glycol monolaurate (293 mg mixture) in a soft gelatin capsule. According to its label, the testosterone undecanoate is co-absorbed with a lipophilic solvent from the intestine into the lymphatic system, thus circumventing the first-pass inactivation by the liver. During absorption testosterone undecanoate is partly reduced to dihydrotestosterone undecanoate. From the lymphatic system it is released into the plasma.

In plasma and tissues both testosterone undecanoate and dihydrotestosterone undecanoate are hydrolyzed to yield the natural male androgens testosterone and dihydrotestosterone. The formulation should however always be taken with a normal meal to ensure absorption as the absorption of testosterone undecanoate. Thus the absorption is extremely dependent on food intake which makes absorption variable and often inadequate. According to the Andriol® label, the oral bioavailability of testosterone undecanoate in a patient in a fed state is more than 50 times that of a patient in a fasted state. The capsules must therefore be taken with the morning and evening meal. Due to this food effect, oral testosterone undecanoate is not a suitable therapy for patients who have a low food or low fat intake, such as many elderly patients. Additionally, one of the main draw backs of this oral formulation is the variability in absorption and thereby unreliable oral bioavailability and fluctuation in serum levels which results in unreliable efficacy.

To be successful in drug formulations targeted for lymphatic absorption the API has to have a high Log P value and a high solubility in lipids. In the case of TU both these criteria are met and therefore TU is a good candidate for lymphatic absorption.

Schnabel et al. (Clin. Endocrin., vol. 66, 579-585, 2007) found that for effective lymphatic absorption of Andriol® Testocaps in humans, 19 g of food lipid was found to be needed, whereas 5 g of lipid led to poor absorption. Two Andriol® Testocaps corresponding to totally 80 mg TU were dosed in the study. The dosed capsules contained total 586 mg of castor oil:propylene glycol monolaurate (60:40 w/w) corresponding to only 350 mg long chain fat. From the study it was also concluded that inter subject variation was inversely correlated to lipid intake. At high lipid intake the bioavailability was found to be fairly reproducible whereas the variation was very high at low fat intake (up to 40% for AUC).

Lymphatic absorption is a complex process which will be influenced by the formulation as well as the food taken at the time of dosing. In literature it is described that lipophillic drugs with high Log P values can be absorbed into the enterocytes and be incorporated into lipoproteins inside the enterocytes. The drug has to dissolve in the GI-tract and pass the unstirred water layer prior to absorption into the enterocytes. To achieve this, drugs can "hide" in micelles formed either from lipid digestion products and bile or from surfactants present in the formulation.

Fatty acids and monoglycerides are taken up at the same time and re-synthesized to triglycerides, which forms the center of the lipoproteins. Those lipoproteins are then exocytosed from the enterocytes into the lumen and have to diffuse to the lymph. This transport of drug can be increased by increasing the flow of lipoproteins, which again will depend on the amount of lipids in the gut.

As fatty acids and monoglycerides are critical to this absorption mechanism, they have to be supplied either from food or from the formulation of the drug. This can be in the form of fats, monoglycerides or fatty acids. Fats need to be digested to fatty acids and monoglycerides by enzymes in stomach and intestine to be absorbed. Better dispersion to small droplets will help digestion by increasing surface of fat particles giving access for enzymes. In literature different combinations of fats, glycerides or fatty acids have been tested for influence on lymphatic absorption. No general agreement has been reached to which combinations are optimal but from literature it is clear that the fat composition play an important role as well as the amount of fat taken. Khoo et al (Pharm. Res., vol. 20, 1460-1464, 2003) demonstrated that a formulated fat composition of only 600 mg was enough to trigger lipid metabolism in the GI tract and induce high lymphatic absorption of the compound Halofantrine in fasted dogs. Further, the exogenous lipid supplied in the formulation was demonstrated to induce transport of endogenous lipid, as a 5-fold flow of lipid was found to be transported to the lymph, compared to the lipid from the formulation.

SUMMARY OF THE INVENTION

The present inventors have realized that a certain fat composition comprising monoglycerides of long chain fatty acids can support a testosterone component having a log P of at least 5 so as to achieve lymphatic absorption of the testosterone component in fed as well as in fasted state, and further achieve a high oral bioavailability of testosterone and at the same time a low variability in absorption.

The present invention relates to a pharmaceutical formulation comprising a testosterone component having a log P of at least 5 (preferably testosterone undecanoate) and carrying enough fat in a vehicle to achieve lymphatic absorption of the testosterone component in fed as well as in fasted state.

Accordingly, the present invention relates to a pharmaceutical composition comprising a testosterone derivative having a log P of at least 5 and a vehicle, wherein the vehicle comprises (a) a fat component in an amount sufficient to achieve lymphatic absorption in a mammal, wherein the fat component comprises a mono- or tri-glyceride of long chain fatty acids.

In a further aspect the present invention relates to a composition comprising a testosterone derivative having a log p of at least 5 and a vehicle, wherein the vehicle comprises (a) a fat component in an amount sufficient to achieve lymphatic absorption in a mammal, wherein the fat component comprises a mono- or tri-glyceride of long chain fatty acids for use in treatment of conditions associated with a deficiency or absence of endogenous testosterone in a mammal in need thereof. In particular, the composition is administered orally as a testosterone replacement therapy.

In a still further aspect the present invention relates to a method of treating a condition associated with a deficiency or absence of endogenous testosterone in a mammal in need thereof, comprising administration of a composition comprising a testosterone derivative having a log p of at least 5 and a vehicle, wherein the vehicle comprises (a) a fat component in an amount sufficient to achieve lymphatic absorption in a mammal, wherein the fat component comprises a monoglyceride of long chain fatty acids. In particular, the composition is administered orally as a testosterone replacement therapy.

Listed below are further embodiments of the present invention:

Embodiment 1

A pharmaceutical composition comprising a testosterone derivative having a log P of at least 5 and a vehicle, wherein the vehicle comprises (a) a fat component in an amount sufficient to achieve lymphatic absorption in a mammal, wherein the fat component comprises a mono- or tri-glyceride or a mono- and tri-glyceride of long chain fatty acids.

2. The composition of embodiment 1 wherein the vehicle further comprises (b) a hydrophilic surfactant wherein the ratio (a):(b) is from about 10:1 to about 1:2.

3. The composition of any one of the preceding embodiments wherein the fat component comprises a monoglycerid and a triglyceride of long chain fatty acids, wherein the weight ratio of triglycerides to monoglycerides is in a range from about 2.8:1 to about 1:5.

4. The composition of any one of the preceding embodiments wherein the fat component is present in an amount sufficient to enhance or promote intestinal lymphatic transport of the testosterone derivative upon oral administration in the fasted state as well as in fed state, compared to a composition without the fat component.

5. The composition of any one of the preceding embodiments wherein the fat component is substantially free of peppermint oil and/or borage oil.

6. The composition of any one of the preceding embodiments wherein the amount of fat component is at least about 500 mg, such as from 500 mg to 1200 mg.

7. The composition of any one of the preceding embodiments wherein composition exhibits an $AUC_{(0\text{-}inf)(fasted)}/AUC_{(0\text{-}inf)(fed)}$ of at least about 0.4.

8. The composition of any one of the preceding embodiments wherein the ratio of (a):(b) ranges from about 4:1 to about 1:2.

9. The composition of any one of the preceding embodiments wherein the long chain fatty acids in the monoglycerides are selected from fatty acid chains having from 14 to 22 carbon atoms, such as linoleic acid, oleic acid, palmitic acid, linoleic acid, or stearic acid.

10. The composition of any one of the preceding embodiments 2-9 wherein the long chain fatty acids in the triglycerides are selected from fatty acid chains having from 14 to 22 carbon atoms, such as linoleic acid, oleic acid, palmitic acid, linoleic acid, or stearic acid.

11. The composition of any one of the preceding embodiments 2-9 wherein the fat component comprising a triglyceride of long chain fatty acids is selected from a naturally derived oil, such as soybean oil, olive oil, sesame oil, safflower oil, peanut oil, rapeseed oil, sunflower oil, coconut oil, corn oil, sunflower seed oil, cotton seed oil, palm oil, arachis oil, as well as mono and di glycerides of the aforementioned oils, glycerol mono-oleate, glyceryl monolinoleate or any combination thereof.

12. The composition of any one of the preceding embodiments wherein the fat component does not comprise any triglyceride but only monoglyceride such as glycerol monooleate.

13. The composition of any of the preceding embodiments, wherein the composition is self-emulsifying.

14. The composition of any of the preceding embodiments, wherein the composition, upon dilution in purified water, forms droplets which a d50 of less than about 40 micrometer, such as less than about 20 micrometer, less than about 10 micrometer, or less than about 5 micrometer.

15. The composition of any one of the preceding embodiments wherein the testosterone derivative is in a solid core, such as a tablet core.

16. The composition of embodiment 15 wherein the vehicle is loaded into the solid core.

17. The composition of embodiment 16 wherein the testosterone derivative is dissolved in the vehicle and loaded into the solid core.

18. The composition of any one of the preceding embodiments 15-17 wherein the solid dosage form is a compressed or molded tablet having a hardness of from about 20 N to about 150 N.

19. The composition of embodiment 1 being selected from a liquid, a gel, a granula, a capsule or tablet.

20. The composition of any one of the preceding embodiments wherein the testosterone derivative is a prodrug of testosterone, such as an ester, e.g. testosterone undecanoate, testosterone enathate, testosterone oleate, or testosterone palmitate.
21. The composition of embodiment 20, wherein at least about 95% by weight of the testosterone derivative, such as testosterone undecanoate, is present in the composition after 2 years of storage at 25° C. and 60% relative humidity.
22. The composition of any one of the preceding embodiments wherein the testosterone derivative is present in an amount from about 0.5% to about 20% and typically from about 1 to about 10% by weight based on 100% total weight of the composition.
23. The composition of any one of the preceding embodiments wherein the testosterone derivative is testosterone undecanoate in an amount of from about 10 mg to 200 mg, such as from about 30 mg to about 60 mg, e.g. 40 mg.
24. The composition of any one of the preceding embodiments wherein the hydrophilic surfactant is selected from hydrogenated castor oil ethoxylates, polysorbates or any other hydrophilic surfactant with a Hydrophile-Lipophile Balance (HLB) value of 10 or higher, and any combination thereof.
25. The composition of any one of the preceding embodiments for use in treatment of conditions associated with a deficiency or absence of endogenous testosterone in a mammal in need thereof.
26. The composition of embodiment 25 wherein the composition is administered orally as a testosterone replacement therapy.
27. A method of treating a condition associated with a deficiency or absence of endogenous testosterone in a mammal in need thereof, comprising administration of the composition of any one of the preceding embodiments 1-26.
28. The method of embodiment 27 wherein the composition is administered orally as a testosterone replacement therapy.
29. A vehicle comprising a1) a fat component comprising a mono- or tri-glyceride or a mono- and tri-glyceride of long chain fatty acids.
30. The vehicle of embodiment 29 wherein the weight ratio of triglycerides to monoglycerides is in a range from about 2.8:1 to about 1:5
31. The vehicle of embodiment 29 or 30 wherein the vehicle further comprises (b1) a hydrophilic surfactant.
32. The vehicle of embodiment 31 wherein the ratio (a1):(b1) is from about 10:1 to about 1:2.

Further objects and advantages of the present invention will appear from the following description, and claims.

DESCRIPTION OF THE INVENTION

It is speculated whether effective lymphatic absorption of molecules with high log P and high solubility in triglycerides can be achieved with low amounts of lipid relevant for single dose formulations.

Optimizing the lymphatic absorption of Testosterone Undecanoate can be accomplished in two ways.

First solubilization of fat components into micelles can be achieved by proper selection of surfactants. Solubilization will improve both the rate of digestion of fat and the amount of drug and fat transported over the unstirred water layer. Solubilization of drug and formulation is part of the technology concept.

Secondly, through the selection of lipids which trigger lipid metabolism in the GI tract and induce release of the drug into the lymphatic system. The contrast between the reported data from Khoo et al [1] and Schnabel et al [2] suggests that both fat composition and amount of fat can be improved compared to the TU formulation from Andriol® Testocaps. The amount of fat is an issue especially if the drug is taken in fasted state, and if the fat composition is not optimal or the amount is too low, variation in absorption will be the expected result.

The maximal amount of lymphatic absorbed TU can be estimated from the solubility of Testosterone Undecanoate in triglyceride and the transported triglyceride (Int. J. Pharm., vol. 34, 175-178, 1986). This can be estimated to ~100 mg (25% (of solubility in triglyceride)×120 mg/g (solubility in triglyceride)×3.5 g triglyceride/10 h (transported triglyceride with formulation of 600 mg fat)).

It is most likely that a more efficient formulation based on incorporation of larger amount of selected solubilizers and fats will result in an increase in bioavailability and/or decrease in variability. Further, a reduction in food effect is achieved by an increase in bioavailability and a decrease in variability.

The present invention relates to a pharmaceutical composition comprising a testosterone derivative having a log p of at least 5 and a vehicle, wherein the vehicle comprises (a) a fat component in an amount sufficient to achieve lymphatic absorption in a mammal, wherein the fat component comprises a mono- or tri-glyceride of long chain fatty acids.

In an embodiment the vehicle further comprises (b) a hydrophilic surfactant, wherein the ratio (a):(b) is from about 10:1 to about 1:2, such as from about 4:1 to about 1:2. The ratio (a):(b) may range from about 40:60 to about 80:20, such as from about 50:50 to about 70:30. In one embodiment, the ratio (a):(b) ranges from about 55:45 to about 65:35, such as about 60:40.

The hydrophilic surfactant may be any described herein. Suitable hydrophilic surfactants include hydrogenated castor oil ethoxylates (such as Polyoxyl 35 castor oil), polysorbates (such as polysorbate 80) or any other hydrophilic surfactant with a Hydrophile-Lipophile Balance (HLB) value of 10 or higher, and any combination of any of the foregoing.

In another embodiment the fat component further comprises a triglyceride of long chain fatty acids, wherein the weight ratio of triglycerides to monoglycerides is in a range from about 2.8:1 to about 1:5. When one or more triglycerides are present in the fat component, the ratio of triglyceride to monoglyceride may, for instance, range from about 2:1 to about 1:5, such as from about 3:2 to about 1:4. In one embodiment, the ratio is from about 1:1 to about 1:3.

In a further embodiment the fat component is present in an amount sufficient to enhance or promote intestinal lymphatic transport of the testosterone derivative upon oral administration in the fasted state as well as in fed state, compared to a composition without the fat component.

In a still further embodiment the fat component is substantially free (e.g., contains less than 1% by weight) of peppermint oil and/or borage oil. In another embodiment, the formulation is free of peppermint oil and/or borage oil.

In a further embodiment the amount of fat component is at least about 500 mg, such as at least 600 mg, at least 700 mg, at least 800 mg, at least 1000 mg, such as from about 500 mg to about 1000 mg.

In a still further embodiment the composition exhibits an $AUC_{(0-inf)(fasted)}/AUC_{(0-inf)(fed)}$ of at least about 0.4. This formulation exhibits enhanced bioavailability and a reduced food effect. Without being bound by or limited to theory, it is believed that the formulation achieves this result by enhancing absorption of the testosterone by the intestinal lymphatic system rather than by way of portal circulation. In a preferred embodiment, the formulation exhibits an $AUC_{0-inf(fasted)}/AUC_{0-inf(fed)}$ (i.e., $AUC_{(0-inf)(fasted)}/AUC_{(0-inf)(fed)}$) of at least about 0.5. In further preferred embodiments, the formulation exhibits an AUC0-inf (fasted)/AUC0-inf(fed) of at least about 0.6, at least about 0.7, or at least about 0.8.

The long chain fatty acids in the monoglycerides and triglycerides may have range in length from 14 to 24 carbon atoms.

In a further embodiment the long chain fatty acids in the monoglycerides are selected from fatty acid chains having from 14 to 22 carbon atoms, such as from 16 to 20 carbon atoms.

In a still further embodiment the long chain fatty acids in the triglycerides are selected from fatty acid chains having from 14 to 22 carbon atoms, such as from 16 to 20 carbon atoms.

Suitable fatty acids for the monoglycerides and triglycerides include, but are not limited to, (A) linoleic acid (18:2), (B) oleic acid (18:1), (C) palmitic acid (16), (D) linoleic acid (18:3), and (E) stearic (18:0). (The first number in the parentheticals in the prior sentence refers to the number of carbon atoms in the fatty acid chain, and the second number refers to the degree of unsaturation (e.g., 1 refers to 1 double bond).)

When triglycerides are present in the fat component they may typically be present as oils. In a further embodiment the fat component comprising a triglyceride of long chain fatty acids is selected from an oil such as soybean oil, olive oil, sesame oil, safflower oil, or any combination thereof.

Sometimes the fat component does not comprise any triglyceride but only monoglyceride such as glycerol monooleate.

In another embodiment, the fat component comprises monoglycerides and triglycerides.

In a further embodiment, the fat component is selected from olive oil.

In a still further embodiment, the fat component is selected from soybean oil.

In a further embodiment, the fat component is selected from a mixture of olive oil and glycerol mono oleate.

In a still further embodiment, the fat component is selected from a mixture of soybean oil and glycerol mono oleate.

The vehicle formulation may be a liquid and it may also be self-emulsifying when introduced to aqueous media. In a certain embodiment, the composition, upon dilution in purified water, forms droplets with a $d_{50}$ of less than about 50 µm. In a further embodiment the composition, upon dilution in purified water, forms droplets with a $d_{50}$ of less than about 40 micrometer, such as less than about 20 micrometer, less than about 10 micrometer, or less than about 5 micrometer, such as droplets having a $d_{50}$ ranging from about 0.01 to about 40 µm, such as from about 0.1 to about 20 µm.

In a further embodiment the testosterone derivative is in a solid core, such as a tablet core.

In a still further embodiment the vehicle is loaded into the solid core. When the composition is in the form of a tablet, the testosterone derivative can optionally be dissolved in the vehicle or the testosterone derivative can optionally be full or partly included in the tablet core before loading of the vehicle. In an embodiment the testosterone derivative is dissolved in the vehicle and loaded into the solid core.

When the dosage form is solid it may be a compressed or molded tablet having a hardness of from about 20 N to about 150 N.

In a further embodiment the testosterone derivative (having a log p of at least 5) is a prodrug of testosterone, such as an ester, e.g. testosterone undecanoate, testosterone enathate, testosterone oleate, or testosterone palmitate. Typically, the testosterone derivative is testosterone undecanoate. When the testosterone derivative is testosterone undecanoate it is typically present in each dose (tablet, capsule or prescribed liquid, gel or granules) in an amount of from about 10 mg to 200 mg, for example, from about 10 to about 120 mg, from about 20 to about 120 mg, from about 10 to about 150 mg, from about 20 to about 150 mg, or from about 15 to about 80 mg. In further embodiments, the solid oral dosage form includes about 20, about 40, about 50, about 60, about 75, or about 80 mg of the testosterone undecanoate.

The present pharmaceutical composition is highly stable and at least about 95% by weight of the testosterone derivative, such as testosterone undecanoate, is present in the composition after 2 years of storage at 25° C. and 60% relative humidity.

In a further embodiment the testosterone derivative is present in an amount from about 0.5% to about 20% and typically from about 1 to about 10% by weight based on 100% total weight of the composition. Moreover, the testosterone derivative may be present in the composition at from about 3 to about 15%, based upon the total weight of the composition. For example, the composition may include from about 1 to about 12% or from about 1 to about 8% of the testosterone derivative, based upon the total weight of the composition.

The composition of the present invention may be selected from a liquid, a gel, a granula, a capsule or tablet. In one embodiment, the composition, e.g. oral, could be a liquid. In such case the testosterone derivative is solubilized in the vehicle. In another embodiment, the composition, e.g. oral, is a capsule, and in this case the testosterone derivative is solubilized in the vehicle and is filled into soft or hard capsules.

In a further aspect the present invention relates to an oral dosage form, such as a solid oral dosage form, comprising the pharmaceutical composition of the invention. The composition may be incorporated into a solid oral dosage form having a solid carrier as discussed below. The testosterone derivative can be solubilized in the vehicle or it can be fully or partly added to the solid carrier before loading of the carrier.

Yet another embodiment is an oral tablet comprising (i) a porous excipient, (ii) optionally a binder or release enhancing agent, (iii) optionally a disintegrant or other standard tablet excipients, (iv) a composition of the present invention.

The solid oral dosage form may be prepared by preparing a granulate of the porous excipient and optionally a binder and/or release enhancing agent, and preparing a loadable tablet comprising a porous excipient, optionally a binder, optionally a release enhancing agent, optionally a disintegrant and optionally other normal tablet excipients (binders, lubricants, flow enhancers etc), and loading the mixture of a testosterone derivative in the vehicle into the tablets, until the testosterone derivative is loaded, for example, to about 50% or more (e.g., 70% or more) of the loading capacity.

The loading may be performed by placing the tablet in an excess amount of the testosterone derivative in the vehicle for a sufficient amount of time. In an embodiment, the loading is performed under pressure. The time period of loading the testosterone undecanoate may be from about 15 minutes to about 10 hours.

Yet another embodiment is a method of delivering a testosterone component to the systemic circulation through the lymphatic transport system by the oral administration to a mammal subject of a solid oral dosage form or oral pharmaceutical formulation of the present invention.

Preferably, the solid oral dosage form includes at least about 300 mg (e.g., at least about 400 mg, at least about 500 mg, at least about 550 mg, or at least about 600 mg) of the long chain lipids. In a further embodiment, the total content of long chain lipids in the solid oral dosage form ranges from about 600 to about 800 mg, such as from about 600 to about 700 mg.

A typical embodiment of the solid oral dosage form comprises (A) a solid carrier comprising porous Silicon dioxide; and (B) a mixture comprising from about 10 to about 120 mg of testosterone undecanoate in a vehicle comprising (a) a fat component in an amount sufficient to achieve lymphatic absorption in a mammal, wherein the fat component comprises a monoglyceride of long chain fatty acids, and (ii) optionally, one or more hydrophilic surfactants, wherein (ai) the mixture is loaded in the porous Silicon dioxide, and (bi) the solid oral dosage form comprises from about 600 to about 1000 mg of long chain lipids (e.g., from about 600 to about 800 mg).

As explained herein the pharmaceutical composition of the present invention may be administered so as to avoid the requirement of orally administering a testosterone derivative (such as testosterone undecanoate) in the fed state.

In a further aspect the present invention relates to a method of preparing the pharmaceutical composition of the invention comprising formulating the testosterone derivative with a vehicle comprising a fat component in an amount sufficient to achieve lymphatic absorption in a mammal, such that oral administration of the formulation in the fed or fasted state facilitates delivery of the testosterone derivative to the systemic circulation through the lymphatic transport system.

In a further aspect the present invention relates to a composition comprising a testosterone derivative having a log p of at least 5 and a vehicle, wherein the vehicle comprises (a) a fat component in an amount sufficient to achieve lymphatic absorption in a mammal, wherein the fat component comprises a monoglyceride of long chain fatty acids for use in treatment of conditions associated with a deficiency or absence of endogenous testosterone in a mammal in need thereof. In particular, the composition is administered orally as a testosterone replacement therapy. The testosterone replacement therapy may be for a primary or secondary hypogonadal disorder, such as eunuchoidism, hypopituitarism, endocrine impotence, decreased libido or infertility due to disorders of spermatogenesis.

In a still further aspect the present invention relates to a method of treating a condition associated with a deficiency or absence of endogenous testosterone in a mammal in need thereof, comprising administration of a composition comprising a testosterone derivative having a log p of at least 5 and a vehicle, wherein the vehicle comprises (a) a fat component in an amount sufficient to achieve lymphatic absorption in a mammal, wherein the fat component comprises a monoglyceride of long chain fatty acids. In particular, the composition is administered orally as a testosterone replacement therapy. The testosterone replacement therapy may be for a primary or secondary hypogonadal disorder, such as eunuchoidism, hypopituitarism, endocrine impotence, decreased libido or infertility due to disorders of spermatogenesis.

In particular a method of testosterone replacement therapy, comprising orally administering to a mammal subject in need thereof (e.g., in the fasted state) a solid oral dosage form or oral pharmaceutical composition of the present invention, leads to improved treatment and compliance.

The solid oral dosage form of the present invention can provide a number of advantages over conventional methods for the delivery of a testosterone derivative within the subject. For example, the solid oral dosage forms comprising the composition of the present invention can provide sufficient bioavailability of testosterone derivative regardless of whether the subject is in the fed or fasted state. Accordingly, in the methods of treatment described, the solid oral dosage forms may be administered in the fed or fasted state. This is a particular advantage when treating an elderly male population, who typically do not eat a sufficient amount to achieve satisfactory absorption of testosterone from conventional formulations. In addition, the solid oral dosage forms of the present invention may substantially avoid passage of the testosterone to the liver via the portal blood.

The formulation in the form of a tablet may have several advantages, including the possibility of including functional coatings, oxygen protection, targeted release, use of excipients which are not compatible with capsules, simpler production process, and use of standard equipment.

Testosterone Derivative

The testosterone derivative may be either a prodrug or a salt of testosterone as explained above. The derivative of testosterone should have a log P of at least 5. Preferably, the testosterone derivative has a log P of at least 6. The testosterone derivative may be present at a concentration of about 10 mg to about 320 mg (based on the total amount of the testosterone derivative in each dose). For example the concentration may be from about 10 to about 160 mg, from about 20 to about 80 mg, from about 30 to about 50 mg. For example the concentration can be about 20, 30, 40, 50, 60, 70, 80 mg.

As explained above the testosterone derivative may be solubilized in the vehicle before loading into the solid carrier of the solid oral dosage form or the testosterone derivative may be solubilized in the vehicle before loading into a capsule.

In a typical embodiment the oral dosage form includes the testosterone derivate as partly or fully incorporated into the tablet core together with a solid carrier and the vehicle is loaded into this tablet core to create the solid oral dosage form. The vehicle loaded can either be without or having some of the testosterone derivative solubilized.

In a further embodiment of the composition the testosterone derivative is testosterone undecanoate and at least 25% of the testosterone undecanoate is dissolved and solubilized from said composition within 180 minutes, as determined by USP XXIII Paddle Method II using water containing 2% SLS at 37° C. as the dissolution media and 100 rpm as the stirring rate.

The Vehicle

The vehicle may be composed from lipids and optionally hydrophilic surfactants as explained herein.

By lipids is understood to refer to, if not indicated otherwise, saturated, mono-unsaturated and polyunsaturated fatty acids and derivatives thereof. Derivatives include esters such as mono-, di- and triglycerides, as well as phospholipids or other glyceride esters.

The lipids may be composed of long chain fatty acids of from $C_{14}$ to $C_{22}$ or a derivative thereof, indicating from 14 carbon atoms in the fatty acid chain up to 22 carbon atoms in the fatty acid chain. The fatty acid may be a saturated, monounsaturated or polyunsaturated fatty acid or a derivative thereof. Each chain in the fatty acid or glyceride may have, for example, 0, 1, 2, or 3 double bonds. The term "long chain lipid" refers to long chain (i.e., $C_{14}$ or greater, such as $C_{14}$-$C_{22}$ or $C_{16}$-$C_{18}$) fatty acids, as well as derivatives of long chain fatty acids. Examples of suitable lipids for the vehicle include those which stimulate the production of endogenous lipid such as those described in U.S. Pat. No. 6,096,338, the entire contents of which is incorporated herein by reference.

The lipids may be formulated with the testosterone undecanoate in the form of a naturally derived oil, such as soybean oil, olive oil, peanut oil, rapeseed oil, sunflower oil, coconut oil, corn oil, sunflower seed oil, cotton seed oil, palm oil, arachis oil, safflower oil, or a combination thereof. Other suitable lipids include, but are not limited to, mono and di glycerides of the aforementioned oils, glycerol monooleate, glyceryl monolinoleate, and any combination of any of the foregoing.

The lipid(s) may be used alone or in combination with one or more. In one embodiment, the lipids alone or in combination with a surfactant stimulate the production of endogenous lipid or otherwise enhance or promote lymphatic transport of the testosterone. For instance, the vehicle may be selected from long chain lipids, and long chain lipids in combination with a hydrophilic surfactant.

Examples of surfactants which may be suitable include esters of mono or di-glycerides, (such as the acetic, succinic, lactic, citric or tartaric esters), propylene glycol, mono or di-esters of fatty acids, polyglycerol esters of fatty acids, acid and ester ethoxylates of fatty acids, sorbitan esters of fatty acids, transesterification products of natural or hydrogenated vegetable oil triglycerides and polyalkylene polyol, alcohol ethoxylates, polyoxyethylene or polyoxypropylene copolymers, phospholipids, polyoxyethylene sorbitan fatty acid derivatives (such as polysorbates, e.g., polysorbate 80), castor oil or hydrogenated castor oil ethoxylates, for example Polyoxyl 35 castor oil/Cremophor EL™, anionic surfactants, such as sodium lauryl sulphate or sodium oleate, alkylphenol surfactants, as well as mixtures of such surfactants. In such combinations, the surfactant may act to assist uptake of the fatty acid from the intestinal lumen. In one embodiment, a hydrophilic surfactant with an HLB value >10, such as Cremophor EL™, is used, optionally in combination with a co-surfactant, which may be a hydrophobic surfactant with a HLB value <10.

Typically, the vehicle comprises a lipid selected from olive oil, soybean oil, glycerol monooleate, and any combination of any of the foregoing. In one embodiment, the vehicle comprises olive oil and glycerol monooleate. In another embodiment, the vehicle comprises soybean oil and glycerol monooleate.

When, the vehicle comprises a surfactant it is typically selected from polysorbate 80, polyoxyl 35 castor oil, and any combination of any of the foregoing.

In an embodiment, the vehicle comprises (a) the lipids olive oil and glycerol monooleate and (b) the surfactant polyoxyl 35 castor oil.

In a preferred embodiment, the vehicle comprises (a) the lipids soybean oil and glycerol monooleate, and (b) the surfactant polyoxyl 35 castor oil.

In another preferred embodiment, the vehicle comprises (a) the lipids olive oil and glycerol monooleate, and (b) the surfactants polysorbate 80 and polyoxyl 35 castor oil.

In a further embodiment, the vehicle comprises a mixture of (a) long chain lipids, and (b) surfactants (hydrophilic surfactants). The weight ratio of (a):(b) may range from about 8:1 to about 1:6. For instance, the weight ratio of (a):(b) may be from about 4:1 to about 1:2. In one embodiment, the weight ratio of (a):(b) ranges from about 3:1 to about 1:2. In another embodiment, the weight ratio of (a):(b) ranges from about 2:1 to about 1:1. In one preferred embodiment, the weight ratio of (a):(b) is about 3:2.

The vehicle is preferably present in an amount sufficient to enhance or promote lymphatic transport of the testosterone undecanoate. See Porter et al., *Pharm. Res.* 20(9):1460-1465 (2003). In one embodiment, the fat component is present in an amount of at least about 500 mg. For example, the amount can be from about 0.05 to about 4 g, such as from about 0.1 to about 1 g, corresponding to an amount which could be readily incorporated into a single solid oral dosage form. In another embodiment, the fat component is present in an amount that is at least about 600 mg, for example, from about 600 mg to about 1200 mg or from about 600 mg to about 1000 mg.

The vehicle may be formulated as lipid based emulsions or micro emulsions, or self-emulsifying or self-micro emulsifying formulations. Self-emulsifying and self-micro emulsifying formulations are those which spontaneously form emulsions or micro emulsions on contact of the contents of the solid oral dosage form with the gastric or intestinal fluids and which are commonly termed self-emulsifying drug delivery systems (SEDDS) or self-micro emulsifying drug delivery systems (SMEDDS). The testosterone derivative is intended to be solubilized in the vehicle either before or after loading of the vehicle into the oral dosage form.

The Solid Carrier

The solid carrier comprises a porous excipient and optionally a binder and/or a disintegrant. The solid carrier may be inert or alternatively the solid carrier may have incorporated the testosterone component in part or full. The solid carrier can be in the form of a tablet. The solid carrier is capable of loading a vehicle.

When the solid carrier is in the form of granules, the median particle size of the granules may range from about 5 microns to about 600 microns, for example from about 10 to about 300 microns. Granules may be compressed to form a tablet which is used as the solid carrier.

The Porous Excipient

The porous excipient typically forms the bulk of the solid carrier. The porous excipient (and the solid carrier) has a porosity of, for example, greater than about 10% v/v, such as greater than about 15% v/v, greater than about 20% v/v, greater than about 30% v/v or greater than about 30% v/v. In a preferred embodiment, the porosity is greater than about 30% v/v, for example, from about 30 to about 50% v/v. In another embodiment, the porosity is up to about 97% (e.g., from about 90 to about 94%) (such as Zeopharm or Aeroperl).

The porous excipient may have a median particle size of from about 5 microns to about 600 microns, for example from about 10 to about 300 microns. In one embodiment, the porous excipient may have a particle size of from about 10 microns to about 150 microns.

The solid carrier may include the porous excipient at a concentration of about 20% w/w or more, such as about 25% w/w or more, about 30% w/w or more, about 35% w/w or more, about 40% w/w or more, about 45% w/w or more, about 50 w/w or more, about 60% w/w or more, about 70% or more, about 80% or more, about 90% or more, about 95% or more, or about 98% or more. In additional embodiments, the porous excipient is present at a concentration of from about 20% to about 95% w/w, such as from about 30% to about 90% w/w, from about 50% to about 90% w/w, from about 60% to about 90% w/w, from about 70% to about 90% w/w, from about 65% to about 85% w/w, from about 75% to about 85% w/w or from about 70% to about 80% w/w, based on 100% total weight of the solid carrier.

Examples of porous excipients include, but are not limited to, metal oxides, metal silicates, metal carbonates, metal phosphates, metal sulfates, sugar alcohols, sugars, celluloses, cellulose derivatives, and any combination of those. In a preferred embodiment, the porous excipient is a metal silicate, e.g., a silicon dioxide, such as Zeopharm (available from J.M. Huber Corporation) or Aeroperl (available from Evonik industries). In another preferred embodiment, the porous excipient is a metal oxide, such as magnesium aluminometasilicate Metal oxides include as examples, but are not limited to, magnesium oxide, calcium oxide, zinc oxide, aluminum oxide, titanium dioxide (such as Tronox A-HP-328 and Tronox A-HP-100), silicon dioxides (such as Aerosil, Cab-O-Sil, Syloid, Aeroperl, Sunsil (silicon beads), Zeofree, Zeopharm, Sipernat), and mixtures thereof. In one embodiment, the metal oxide is titanium dioxide, silicon dioxide or a mixture thereof. Silicon dioxides may be subdivided into porous and nonporous silicas.

Metal silicates include as examples, but are not limited to, sodium silicate, potassium silicate, magnesium silicate, calcium silicate including synthetic calcium silicate such as, e.g., Hubersorp, zinc silicate, aluminum silicate, sodium aluminosilicate such as, e.g., Zeolex, magnesium aluminum silicate, magnesium aluminum metasilicate, aluminium metasilicate. The porous excipient may be a hydrous aluminum silicate or alkaline earth metal silicate, such as magnesium aluminum metasilicate (e.g., Neusilin available from Fuji Chemical Co.).

Suitable metal phosphates include, but are not limited to, sodium phosphate, disodium hydrogen phosphate, sodium dihydrogen phosphate, potassium phosphate, dipotassium hydrogen phosphate, potassium dihydrogen phosphate, calcium phosphate, magnesium phosphate, zinc phosphate, aluminum phosphate, and combinations thereof. For example, the porous excipient can be dibasic anhydrous calcium phosphate, dibasic dihydrate calcium phosphate, tribasic calcium phosphate, or a combination thereof.

Exemplary metal sulfates include, e.g, sodium sulfate, sodium hydrogen sulfate, potassium sulfate, potassium hydrogen sulfate, calcium sulfate, magnesium sulfate, zinc sulfate aluminum sulfate, and mixtures thereof.

Exemplary sugar alcohols include, e.g., sorbitol, xylitol, mannitol, maltitol, inositol, and/or it may be a sugar selected from the group consisting of mono-, di- or polysaccharides including saccharose, glucose, fructose, sorbose, xylose, lactose, dextran, dextran derivatives, cyclodextrins, and mixtures thereof.

Exemplary celluloses and cellulose derivatives include, e.g., cellulose, microcrystalline cellulose, cellulose derivatives including porous cellulose beads: cellulose, hydroxypropyl methylcellulose (HPMC), hydroxypropyl cellulose (HPC), methylcellulose, ethylcellulose, sodium carboxymethylcellulose, hydroxyethyl cellulose etc.

Additional Excipients

The solid oral dosage form may further comprise one or more pharmaceutically acceptable excipients. Examples of such excipients include, but are not limited to, fillers, diluents, binders, lubricants, glidants, enhancers, wetting agents, surfactants, antioxidants, metal scavengers, pH-adjusting agents, acidifying agents, alkalizing agents, preservatives, buffering agents, chelating agents, stabilizing agents, coloring agents, complexing agents, emulsifying and/or solubilizing agents, absorption enhancing agents, modify release agents, flavoring agents, taste-masking agents, humectants, and sweetening agents.

Examples of suitable fillers, diluents and/or binders include lactose (e.g. spray-dried lactose, α-lactose, β-lactose), microcrystalline cellulose, hydroxypropylcellulose, hydroxypropyl methylcellulose (HPMC), methylcellulose, hydroxyethylcellulose, sodium carboxymethylcellulose, carboxymethylene, carboxymethylhydroxyethyl cellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate and potassium hydrogen phosphate.

Examples of metal scavengers include, but are not limited to, tartaric acid, citric acid, oxalic acid, EDTA and salts thereof, and DPTA (diethylenetriaminepentaacetic acid) and salts thereof.

Examples of antioxidants include, but are not limited to, BHT, BHA, propyl gallate, tocopherols, TBHQ (t-butyl hydroquinone), and ascorbyl palmitate.

Examples of diluents include, but are not limited to, calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, and sugar.

Examples of binders include, but are not limited to, acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, maltodextrin and pregelatinized starch.

Examples of glidants and lubricants include, but are not limited to, stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, and sodium acetate.

Examples of antioxidants include, but are not limited to, ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, and TPGS or other tocopherol derivatives. The concentration of an antioxidant and/or a stabilizing agent in the tablet may be, for example, from about 0.1% w/w to about 5% w/w (based upon 100% total weight of the unloaded tablet).

The solid oral dosage form may also include one or more components that biochemically modulate metabolism of the testosterone prodrug, such as testosterone undecanoate, to testosterone if a prodrug is being used, and/or metabolism of testosterone to dihydrotestosterone (DHT). For example, natural and synthetic inhibitors of 5α-reductase, which is an enzyme present in enterocytes and other tissues that catalyzes the conversion of testosterone to DHT. Complete or partial inhibition of this conversion may both increase and sustain serum levels of testosterone after oral dosing while concomitantly reducing serum DHT levels. Borage oil, which contains a significant amount of the 5α-reductase inhibitor, gamma-linolenic acid (GLA), is an example of a natural modulator of testosterone undecanoate metabolism. Other than within borage oil, of course, GLA could be added directly as a separate component of the solid oral dosage form of the invention. Many natural inhibitors of 5α-reductase are known in the art (e.g., epigallocatechin gallate, a catechin derived primarily from green tea and saw palmetto extract from berries of the *Serenoa repens* species), all of which may be suitable in the present invention. Non-limiting examples of synthetic 5α-reductase inhibitors suitable for use in the present invention include finasteride and dutasteride.

Solid Oral Dosage Form

The amount of solid carrier in the solid oral dosage form may vary depending on its porosity, as the liquid formulation. The solid dosage form preferably includes at least 600 mg of fats (lipids) and sufficient surfactants to allow for lymphatic absorption in the fasted state.

Since the solid oral dosage form, such as tablet or capsule, is intended for oral ingestion by a mammal, such as a human subject, the solid oral dosage form preferably weighs from about 500 mg to about 5000 mg, such as from about 600 mg to about 2000 mg, or from about 600 mg to about 1500 mg. In one embodiment, the solid oral dosage form weighs from about 700 mg to about 1200 mg.

The solid oral dosage form (e.g., oral tablet) described herein may optionally contain one or more coatings, such as a sub-coating and/or modified release coating (e.g. an enteric coating). The sub-coating may be, e.g., Opadray AMB OY-B. The enteric coating may contain, e.g., Acryl EZE, dimethicone and triethyl citrate.

In one embodiment, the solid oral dosage form does not have a coating. In a preferred embodiment, the solid oral dosage form does not have an enteric coating. In another embodiment, the solid oral dosage form does not have a modified release coating. In a preferred embodiment, the solid oral dosage form provides immediate release of the testosterone derivative. In yet another embodiment, the solid oral dosage form provides extended release of the testosterone derivative.

The solid oral dosage form may be in the form of a tablet. In one embodiment, the tablet is a compressed or molded tablet, e.g., having a hardness of from about 20 N to about 150 N. The hardness of the tablet can be from about 30, 40, or 50 N to about 70, 80, 90 or 100 N.

The oral tablet may include one or more excipients, such as those mentioned above including, but not limited to, flavoring agents, lubricants, binders, preservatives, and disintegrants.

In another embodiment, the solid dosage form comprises granules of the solid carrier, testosterone derivative in the vehicle, and optionally other excipients. The granules may, for example, be filled into a capsule which is administered.

Preparation of the Solid Oral Dosage Forms

The solid oral dosage forms described herein may be formed by (i) preparation of the solid carrier, (ii) preparation of the vehicle, (iii) loading the vehicle into the solid carrier and filling the granule into capsules.

In one embodiment, tablets of the present invention are prepared by (ix) preparation of the solid carrier, (iix) pressing the solid carrier and optionally disintegrants and/or other tablet excipients into loadable tablets, (iiix) preparation of the vehicle, (ivx) loading the vehicle into the loadable tablets.

In one embodiment, the testosterone derivative is part of the carrier, in another embodiment the testosterone derivative is solubilized in the vehicle, and in a third embodiment the testosterone derivative is partly in the carrier and partly solubilized in the vehicle.

The testosterone derivative and vehicle together can be in the form of a self-emulsifying drug delivery system (SEDDS) or a self-micro emulsifying drug delivery systems (SMEDDS). See, for example, International Publication No. WO 2006/000227 and U.S. Publication Nos. 2009/0181083 and 2011/0244031, each of which is incorporated by reference in its entirety.

Step (ix) may be carried out by mixing binder or spraying binder solution onto granules of the porous excipient, granulate the mixture in a high shear mixer and drying the granules to provide the granulate.

The carrier granulate may be mixed with tablet excipients, e.g. disintegrants, lubricants etc. and optionally the testosterone derivative and pressed into tablets.

Preparation of the vehicle is done my simply mixing the components and optionally the testosterone derivative until a clear solution appears.

Loading is performed by immersing the tablet into the vehicle in a surplus of the testosterone derivative, the time period for loading the testosterone derivative is controlled and may range from about 30 minutes to about 5 hours, such as from about 30 minutes to about 1 hour. Loading can also be achieved by pouring the calculated oil mixture onto a bed of tablets, e.g., rotating in some form of a drum In all of the methods above, the granulate comprising a porous excipient and a release enhancing agent may be compacted, such as compressed or molded into a tablet that has a suitable hardness, such as a hardness of about 20 N or more, about 25 N or more, about 30 N or more, about 35 N or more, about 40 N or more, about 45 N or more, about 50 N or more, about 60 N or more, about 70 N or more, about 90 N or more, about 100 N or more. In one embodiment, the hardness of the tablet is from about 30 N to about 150 N, such as from about 30 N to about 100 N.

Methods of Treatment

Testosterone is an endogenous hormone responsible for maintenance of bone density, fat distribution, muscle strength and mass, red blood cell production, libido and sperm production. The testosterone level of male humans peaks during adolescence before gradually declining after 30 years of age. A decreased level of testosterone is known as testosterone deficiency syndrome or hypogonadism.

The dosage forms may be orally administered as a testosterone replacement therapy in conditions associated with a deficiency or absence of endogenous testosterone in subjects in need thereof. The subjects may administer the oral dosage form in the fasted state or the fed state.

The oral testosterone dosage form is used as androgen replacement therapy. Androgen replacement therapy is indicated in males for conditions associated with a deficiency or absence of endogenous testosterone like primary hypogonadism (congenital or acquired) and hypogonadotropic hypogonadism (congenital or acquired). Hypogonadism or low testosterone is a common yet largely under-recognized and under-treated condition. Low testosterone is defined as having a testosterone level below normal (testosterone <300 ng/dL). Men with low testosterone have symptoms of androgen deficiency like depression, reduced libido and low energy and may suffer from anemia, osteoporosis and muscle weakness.

Androgen replacement therapy is used for primary or secondary hypogonadal disorder, such as eunuchoidism, hypopituitarism, endocrine impotence, reduced libido or infertility due to disorders of spermatogenesis. A pharmaceutically effective amount of the dosage form(s) is typically administered.

The oral dosage form may also be administered for ameliorating one or more of the side effects of certain strategies for male contraception. For example, progestin-based male contraception substantially suppresses luteinizing hormone (LH) and folliclestimulating hormone (FSH), and thereby suppresses spermatogenesis, resulting in clinical azoospermia (defined as less than about 1 million sperm/mL semen for 2 consecutive months). However, administration of progestins also has the undesirable side effect of significantly reducing steady-state serum testosterone levels. In such situations, for example, it may be preferable to provide preparations of progestin concomitantly with the testosterone component. In one embodiment, a solid oral dosage according to the invention is provided, comprising progestin in an amount sufficient to substantially suppress LH and FSH production in combination with the testosterone component.

In some embodiments, the pharmaceutical preparation is for oral delivery e.g., once or twice daily. A pharmaceutically effective amount of the oral dosage forms are typically administered in such therapies. The oral dosage forms can be taken by a subject in need of testosterone therapy once every about twelve hours (twice a day) to maintain desirable levels of serum testosterone. In another embodiment, the solid oral dosage form(s) are taken by a subject in need of testosterone therapy once every about twenty-four hours (once a day). In general, desirable testosterone levels are those levels found in a human subject characterized as not having testosterone deficiency.

DEFINITIONS

The term "no food effect" and "absence of food effect" on oral bioavailability refers to when the 90 percent CI for the ratio of population geometric means between fed and fasted treatments, based on log-transformed data, is contained in the equivalence limits of 80-125 percent for AUC0-inf (AUC0-t when appropriate) and Cmax.

The term "fasted state" refers to a state of the subject in which the only lipids, if any, present in the intestine of the subject, apart from any which may have been included in a formulation according to the invention, are endogenous lipids. A reference to the oral administration of a drug or formulation according to the invention to a subject "in the fasted state" is a reference to the oral administration into the digestive system of the subject such that during the uptake into the lymphatic system of a therapeutically effective amount of the drug, the subject is in the fasted state. This generally means that the subject has not taken a meal at least 3 to 4 hours prior to the administration and, depending on the rate of uptake and the efficacy of the drug, no food is taken from 1 to 6 hours after the meal.

The term "fed state" as used herein refers to any state of the subject other than a "fasted state" as described above.

The term "log P" refers to the partition coefficient of a substance. The log P of a substance is the base ten logarithm of the ratio of solubility of the substance in n-octanol to solubility of the substance in water.

The term "HLB" or "HLB value" of a surfactant refers to the Hydrophilic-Lipophilic Balance and is a measure of the degree to which it is hydrophilic or lipophilic, determined by calculating values for the different regions of the molecule. For non ionin surfactants the HLB=20*Mh/M, where M is the molecular mass of the whole molecule and Mh is the molecular mass of the hydrophilic portion of the Molecule. An HLB value of 0 corresponds to a completely lipidphilic/hydrophobic molecule, and a value of 20 corresponds to a completely hydrophilic/lypidphobic molecule.

The term "production of endogenous lipid" as used herein refers to the biosynthesis within the intestinal absorptive cells of lipids, including mono, di or triglycerides and phospholipids, from bio-precursors, which bio-precursors could themselves be lipids or lipid conjugates, such as glycerides. For example the biosynthesis may involve the conversion of a lipid species unable to promote transport of the drug into the lymphatic transport system into a species which can. The term "production of endogenous lipid" may also refer to the translocation of lipid species into the enterocytes from elsewhere, such that the lipid species, or lipid metabolite thereof, is capable of promoting transport of the drug into the lymphatic transport system.

The term "mammal" or "mammal subject" as used herein (are interchangeable) refers to all sorts of mammals, such as humans, horses, pigs, dogs, cats, sheeps, etc.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless other-wise indicated herein or otherwise clearly contradicted by context.

The terms "a" and "an" and "the" and similar referents as used in the context of de-scribing the invention are to be construed to cover both the singular and the plural, unless otherwise indicated herein or clearly contradicted by context. Thus, "a" and "an" and "the" may mean at least one, or one or more.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

EXAMPLES

Further description of the present invention will now be done by the following non-limiting examples. It should be kept clearly in mind that the examples are merely illustrative of the present invention and should not be construed as limiting the scope of the invention in any way, as many variations and equivalents that are encompassed by the present invention will become apparent to those skilled in the art upon reading the present disclosure.

Example 1: Preparation of Oral Testosterone Tablet Formulations

Six oral testosterone formulations were prepared as summarized in Table 1.

TABLE 1

| Formulation | Summary of Components |
| --- | --- |
| D1 | Olive oil:Glycerol Mono-Oleate 1:3 with Polysorbate 80:Polyoxyl 35 castor oil 1:1, 60% fat, Testosterone undecanoate in vehicle adsorbed into loadable tablet |
| D2 | Soybean oil:Glycerol Mono-Oleate 1:1 with Polyoxyl 35 castor oil, 60% fat fat, Testosterone undecanoate in vehicle adsorbed into loadable tablet |
| D3 | Soybean oil:Glycerol Mono-Oleate 1:1 with Polyoxyl 35 castor oil, 80% fat fat, Testosterone undecanoate in vehicle adsorbed into loadable tablet |
| D4 | Soybean oil:Glycerol Mono-Oleate 1:1 with Polyoxyl 35 castor oil, 60% fat fat, Testosterone undecanoate partly (10%) in loadable tablet before loading the vehicle and partly in vehicle adsorbed into loadable tablet |
| D5 | Soybean oil:Glycerol Mono-Oleate 1:1 with Polyoxyl 35 castor oil, 60% fat fat, Testosterone undecanoate in loadable tablet before loading the vehicle |
| D6 | Soybean oil:Glycerol Mono-Oleate 1:1 with Polyoxyl 35 castor oil, 60% fat fat, Testosterone undecanoate in vehicle, filled into capsules |

The Solid Carrier

The Solid Carrier was produced by mixing Silicon dioxide (Zeopharm) with 40% maltodextrin (Lycatab DSH) and moistening the mixture with adequate amount of water in a high shear mixer. After granulation the granules were dried on trays and sieved.

Active solid carrier was prepared by dissolving Testosterone Undecanoate in soybean oil (5% concentration), mixing Silicon dioxide (Zeopharm) with 40% maltodextrin (Lycatab DSH) and moistening the mixture with the testosterone undecanoate solution and adequate amount of water in a high shear mixer. After granulation the granules were dried on trays and sieved.

The carrier composition is given in Table 2.

TABLE 2

| | Solid carriers | | | |
| --- | --- | --- | --- | --- |
| | Inactive Solid carrier | | Active Solid carrier | |
| Raw Material | Weight % | mg/tablet | Weight % | mg/tablet |
| Silicon dioxide (Zeopharm) | 60.0 | 526.2 | 54.8 | 526.2 |
| Maltodextrin (Lycatab DSH) | 40.0 | 350.8 | 0.4 | 350.8 |
| Testosterone Undecanoate | | | 8.3 | 4.0 |
| Soybean oil | | | 36.5 | 80.0 |
| Total | 100.0 | 877.0 | 100.0 | 961.0 |

Inactive Loadable Tablets

Solid carrier prepared as described was mixed with 20% of croscarmellose sodium for 10 minutes. Then 0.5% magnesium stearate was added and mixed for 5 minutes. The mixture was compressed into tablets on a 10×22 mm oval tooling using a Diaf tablet press. The tablet composition is given in Table 3. The tablet hardness was 28N.

Active Loadable Tablets

For full amount of testosterone in loadable core tablet: Solid carrier prepared as described was mixed with 2% of croscarmellose sodium and testosterone undecanoate for 10 minutes. Then 0.5% magnesium stearate was added and mixed for 5 minutes. The mixture was compressed into tablets on a 10×22 mm oval tooling using a Diaf tablet press.

For partial amount of testosterone in loadable core tablet: Active Solid carrier prepared as described was mixed with 2% of croscarmellose sodium for 10 minutes. Then 0.5% magnesium stearate was added and mixed for 5 minutes. The mixture was compressed into tablets on a 10×22 mm oval tooling using a Diaf tablet press.

TABLE 3

| | Loadable tablets | | | | | |
| --- | --- | --- | --- | --- | --- | --- |
| | Inactive loadable tablet core | | Testosterone fully in loadable tablet core | | Testosterone partly in loadable tablet core | |
| Raw Material | Weight % | mg/tablet | Weight % | mg/tablet | Weight % | mg/tablet |
| Solid carrier granulate | 97.56 | 877.0 | 93.40 | 877.0 | | |
| Active Solid carrier granulate | | | | | 97.77 | 961.0 |
| Croscarmellose (Ac-Di-Sol) | 1.95 | 17.54 | 1.87 | 17.54 | 1.78 | 17.54 |
| Testosterone undecanoate | | | 4.26 | 40.00 | | |
| Magnesium stearate | 0.49 | 4.39 | 0.47 | 4.39 | 0.45 | 4.39 |
| Total | 100% | 898.9 | 100% | 938.9 | 100% | 982.9 |

SEDDS Vehicles

Four different SEDDS vehicles (formulations A-D) were prepared to be loaded into the loadable tablets, as shown below in Table 4:

TABLE 4

SEDDS formulations

| Ingredient | Formulation | | | |
|---|---|---|---|---|
| | A | B | C | D |
| SEDDS | | | | |
| Olive oil | 9.00 | | | |
| Soybean oil | | 54.0 | 18.0 | 13.2 |
| Glycerol Mono-Oleate | 27.0 | 54.0 | 18.0 | 18.0 |
| Polysorbate 80 | 12.0 | | | |
| Polyoxyl 35 castor oil | 12.0 | 72.0 | 9.0 | 24.0 |
| Formulation (Testosterone Undecanoate + SEDDS) | | | | |
| Inactive SEDDS for API | 60.0 | 120.0 | 45.0 | 55.2 |
| Testosterone Undecanoate | 2.40 | 4.8 | 2.40 | 2.16 |
| API conc. in SEDDS | 3.85% | 3.85% | 5.88% | 3.77% |

In each case, the oil components were dispersed and mixed to afford a clear mono-phasic placebo vehicle system. Before adding the testosterone undecanoate to formulation B, 60 g was removed for loading of the active loadable tablets (formulation D5).

Following removal of the placebo vehicle, the testosterone undecanoate was dispersed and mixed into the each vehicle system overnight.

Solid Oral Dosage Form

All solid dosage forms were prepared to contain 40 mg of testosterone undecanoate and 600 mg of long chain lipid. The solid dosage forms were prepared as follows Table 5):

(a) Loadable tablets: Tablet loading was achieved by immersing the loadable tablets in the SEDDS vehicle. 20 tablets of each formulation were sorted to ensure homogeneity, and loaded in a 3 liter beaker by floating the tablets in an excess of the SEDDS vehicle and allowing the vehicle to be absorbed into the tablet.

(b) Capsules: The active SEEDS were dispensed into an empty capsule shell by a pipette and the capsules were closed.

Example 2: Preparation of Oral Testosterone Tablet Formulations

Seven oral testosterone formulations were prepared as summarized in Table 6.

TABLE 6

| Formulation | Summary of Components |
|---|---|
| FD1 | Olive oil:Glycerol Mono-Oleate 1:3 with Polysorbate 80:Polyoxyl 35 castor oil 1:1, 60% fat, Testosterone undecanoate in vehicle adsorbed into loadable tablet |
| FD2 | Soybean oil:Glycerol Mono-Oleate 1:1 with Polyoxyl 35 castor oil, 60% fat, Testosterone undecanoate in vehicle adsorbed into loadable tablet |
| FD3 | Soybean oil:Glycerol Mono-Oleate 1:1 with Polyoxyl 35 castor oil, 80% fat, Testosterone undecanoate in vehicle adsorbed into loadable tablet |
| FD4 | Soybean oil:Glycerol Mono-Oleate 1:1 with Polyoxyl 35 castor oil, 60% fat, Testosterone undecanoate partly (10%) in loadable tablet before loading the vehicle and partly in vehicle adsorbed into loadable tablet |
| FD5 | Olive oil:Glycerol Mono-Oleate 65:35 with Polysorbate 80:Polyoxyl 35 castor oil 1:1, 60% fat, Testosterone undecanoate in vehicle adsorbed into loadable tablet |
| FD6 | Glycerol Mono-Oleate with Polyoxyl 35 castor oil, 60% fat, Testosterone undecanoate in vehicle adsorbed into loadable tablet |
| FD7 | Soybean oil:Glycerol Mono-Oleate 1:1 with Polyoxyl 35 castor oil, 60% fat, Testosterone undecanoate in vehicle, filled into capsules |

The Solid Carrier

The Solid Carrier was produced by mixing Colloidal Silicon dioxide (Aeroperl 300) with 10% microcrystalline cellulose (Avicel PH 101) and 10% Hypromellose (Metolose 90SH-100SR), and then granulate the mixture with a solution of Hypromellose (Metolose 90SH-100SR) plus adequate amount of water in a high shear mixer. After granulation the granules were dried in a fluid-bed and sieved.

TABLE 5

Solid Oral Dosage Forms

| Ingredient | Formulation per solid dosage form | | | | | |
|---|---|---|---|---|---|---|
| | D1 | D2 | D3 | D4 | D5 | D6 |
| Formulation (Testosterone Undecanoate + SEDDS) | | | | | | |
| Active SEDDS A | 1040 mg | | | | | |
| Active SEDDS B | | 1040 mg | | | | 1040 mg |
| Active SEDDS C | | | 790 mg | | | |
| Active SEDDS D | | | | 956 mg | | |
| Inactive SEDDS B | | | | | 1000 mg | |
| Inactive loadable tablets | 1 tablet | 1 tablet | 1 tablet | | | |
| Partly active loadable tablets | | | | 1 tablet | | |
| Active loadable tablets | | | | | 1 tablet | |
| Gelatin capsule | | | | | | 1 capsule |

Active solid carrier was prepared by dissolving Testosterone Undecanoate in soybean oil (5% concentration), mixing Colloidal Silicon dioxide (Aeroperl 300) with 10% microcrystalline cellulose (Avicel PH 101) and 10% Hypromellose (Metolose 90SH-100SR), and then granulate the mixture with a solution of Hypromellose (Metolose 90SH-100SR) plus adequate amount of water in a high shear mixer. After granulation the granules were dried in a fluid-bed and sieved.

The carrier composition is given in Table 7.

TABLE 7

| | Solid carriers | | | |
|---|---|---|---|---|
| | Inactive Solid carrier | | Active Solid carrier | |
| Raw Material | Weight % | mg/tablet | Weight % | mg/tablet |
| Silicon dioxide (Zeopharm) | 80.0 | 655.2 | 72.56 | 650.83 |
| Microcrystalline cellulose (Avicel PH101) | 10.0 | 81.9 | 9.07 | 81.35 |
| Hypromellose (Metolose 90SH-100SR) | 10.0 | 81.9 | 9.07 | 81.35 |
| Testosterone Undecanoate | — | — | 0.44 | 3.97 |
| Soybean oil | — | — | 8.86 | 79.49 |
| Total | 100.0 | 819.0 | 100.0 | 897.0 |

Inactive Loadable Tablets

Solid carrier prepared as described was mixed with 2% of croscarmellose sodium for 10 minutes. Then 0.5% magnesium stearate was added and mixed for 5 minutes. The mixture was compressed into tablets on a 10×22 mm oval tooling using a Diaf tablet press. The tablet composition is given in Table 8. The tablet hardness was 34N.

TABLE 8

| | Loadable tablets | | | |
|---|---|---|---|---|
| | Inactive loadable tablet core | | Active loadable tablet core | |
| Raw Material | Weight % | mg/tablet | Weight % | mg/tablet |
| Inactive Solid carrier granulate | 97.50 | 819.00 | | |
| Active Solid carrier granulate | | | 97.50 | 897.00 |
| Croscarmellose sodium (Ac-Di-Sol) | 2.00 | 16.80 | 2.00 | 18.40 |
| Magnesium stearate | 0.50 | 4.20 | 0.50 | 4.60 |
| Total | 100% | 840.0 | 100% | 920.0 |

Active Loadable Tablets

Active Solid carrier was prepared as described was mixed with 2% of croscarmellose sodium for 10 minutes. Then 0.5% magnesium stearate was added, and mixed for 5 minutes. The mixture was compressed into tablets on a 10×22 mm oval tooling using a Diaf tablet press. The tablet composition is given in Table 8. The tablet hardness was 29 N.

SEDDS Vehicles

Six different SEDDS vehicles (formulations A-F) were prepared to be loaded into the loadable tablets, as shown below in Table 9:

TABLE 9

| | SEDDS formulations | | | | | |
|---|---|---|---|---|---|---|
| Ingredient | Formulation | | | | | |
| SEDDS | A | B | C | D | E | F |
| Olive oil | 13.59 | | | | 33.17 | |
| Soybean oil | | 63.02 | 27.99 | 21.51 | | |
| Glycerol Mono-Oleate | 40.5 | 63.06 | 28.01 | 29.35 | 17.87 | 51.09 |
| Polysorbate 80 | 18.02 | | | | 17.01 | |
| Polyoxyl 35 castor oil (Cremophor ELP) | 17.99 | 84.02 | 13.98 | 39.16 | 16.99 | 34.08 |
| Testosterone Undecanoate | 3.5968 | 8.008 | 3.505 | 3.53102 | 3.4044 | 3.39901 |
| API conc. in SEDDS | 3.85% | 3.85% | 4.77% | 3.77% | 3.85% | 3.85% |

In each case, the oil components were weighed out and mixed to obtain a clear mono-phasic placebo vehicle system. Then the testosterone undecanoate was added and mixed into the each vehicle system overnight.

Solid Oral Dosage Form

All solid dosage forms were prepared to contain 40 mg of testosterone undecanoate and 600 mg of long chain lipid. The solid dosage forms were prepared as follows (Table 10):

(a) Loadable tablets: Tablet loading was achieved by placing the loadable tablets in a rotating pan and pour the SEDDS vehicle on top while rotating. Rotation was continued until the tablets had absorbed the SEDDS. 80 tablets of each formulation were loaded.

(b) Capsules: The active SEEDS was dispensed into an empty capsule shell by a syringe and the capsules were closed.

TABLE 10

Solid Oral Dosage Forms

| Formulation | FD1 | FD2 | FD3 | FD4 | FD5 | FD6 | FD7 |
|---|---|---|---|---|---|---|---|
| Inactive tablet core | 80 tablets | 80 tablets | 80 tablets | | 80 tablets | 80 tablets | |
| Active tablet core | | | | 80 tablets | | | |
| Gelatin capsule size 000 | | | | | | | 80 capsules |
| SEDDS A | 83.2 g | | | | | | |
| SEDDS B | | 83.2 g | | | | | 83.2 g |
| SEDDS C | | | 67.2 g | | | | |
| SEDDS D | | | | 76.48 g | | | |
| SEDDS E | | | | | 83.2 g | | |
| SEDDS F | | | | | | 83.2 g | |

Example 3: Single Dose Pharmacokinetic Study in Female Beagle Dogs in the Fasted and Fed State A single dose pharmacokinetic study in female Beagle dogs was performed in fasted and in fed state to demonstrate an increased bioavailability and a reduced variation in absorption as well as a reduced or no food effect compared to Andriol® Capsules.

Testosterone undecanoate was formulated in seven different solid oral dosage forms named FD1 to FD7. The compositions of the FD1 to FD7 are provided in Example 2. Andriol® Capsules were included as comparator. In fasted state the dogs were deprived of food from late afternoon by removing the feeding trough. The food was resumed at 8 hours post dose. In fed state, no fasting procedure was performed. The dogs were fed within 5 min after PO administration of test tablets/capsules or reference capsules.

Pentagastrin was dosed via IM (6 μg/kg, 200 μg/mL in water) 30 min prior to administration of the solid oral dosage form of testosterone undecanoate for all treatment groups. Pentagastrin was administered to ensure low pH in the dog's stomach, which otherwise will not have an as low pH as in humans stomachs. Gastric pH was measured right before pentagastrin dosing and right before testosterone undecanoate dosing.

The fasted state study design was a randomized, balanced, cross-over design and includes 16 female Beagle dogs which were divided into 8 groups corresponding to the number of test formulations. Each formulation was tested in totally 4 dogs with 2 dogs in each group (parallel design). For each group, 2 animals crossed over after 7 days washout total N=4/arm.

In fed state a parallel group study design was used having n=4 female dogs in each group. Only the formulations FD3 and FD7 were tested in fed state in comparison with the comparator FD8. Each formulation was dosed as a single dose of two tablets or capsules of 40 mg testosterone undecanoate i.e. a dose corresponding to 80 mg of testosterone undecanoate regardless of body weight. An oral applicator was used for peroral (PO administration) and the tablet or capsule was put directly on the aditus laryngis of the dog to ensure that the tablets/capsules was not chewed but were swallowed whole. To ensure the complete oral dose was received, the animals received 100 mL of water immediately following the tablet/capsule dosing.

Blood samples (approximately ~0.5 mL) were taken from each animal at each dosing occasion on 10 time points up to 24 hours after dosing (0 (pre-dose), 1, 1.5, 2, 3, 5, 8, 12, 16, 24 h). Samples were placed in tubes containing EDTA (K2) and stored on an ice block until centrifuged at 4° C. to obtain plasma within 15 minutes of sample collection. All samples were stored at approximately −80° C. until bioanalysis were performed. Testosterone undecanoate and testosterone were both measured. At least two standard curves plus 6 QC samples (duplicate at each concentration) were applied during sample analysis for each run. The actual number of standard curves and QC samples depend on the amount of unknown sample.

The PK parameters were determined by non-compartmental model of non-compartmental analysis tool, Pharsight Phoenix WinNonlin® 6.2 software. The pharmacokinetic parameters calculated were i.e. total exposure, or area under the concentration-time curve (AUC0-inf, AUC0-t), Peak exposure (Cmax), Time to peak exposure (Tmax) and half-life (t½). The variation in absorption for each oral solid dosage form was calculated and compared to that of Andriol® capsules in both fed and fasted state. The pharmacokinetic data are provided in the Tables 11 and 12 for testosterone undecanoate and testosterone, respectively.

TABLE 11

Summary of major pharmacokinetic parameters of testosterone undecanoate after oral dose at 80 mg (TU)/animal in female beagle dogs (N = 4)

| | PK parameters | | | | |
|---|---|---|---|---|---|
| | Tmax | Cmax | t½ | AUC0-last | AUCINF |
| Treatment Group | hr | ng/mL | hr | hr * ng/mL | hr * ng/mL |
| | PK parameters of Testosterone Undecanoate in fasted study | | | | |
| FD1 | 1.88 | 483 | 0.801 | 1066 | 1086 |
| FD2 | 1.88 | 962 | 0.487 | 1993 | 2012 |
| FD3 | 2.00 | 1038 | 0.927 | 1981 | 1817 |
| FD4 | 2.25 | 739 | 0.795 | 1855 | 1696 |
| FD5 | 2.25 | 908 | 0.783 | 1797 | 1554 |
| FD6 | 1.75 | 177 | 0.431 | 249 | 194 |
| FD7 | 1.38 | 2710 | 0.438 | 4164 | 4166 |
| Andriol ® | 1.63 | 142 | 0.557 | 205 | 209 |
| | PK parameters of Testosterone Undecanoate in fed study | | | | |
| FD3 | 1.75 | 836 | 1.16 | 1942 | 1992 |
| FD7 | 1.13 | 1372 | 0.839 | 2257 | 2260 |
| Andriol ® | 1.13 | 428 | 1.72 | 963 | 971 |

TABLE 12

Summary of major pharmacokinetic parameters of testosterone after oral dose at 80 mg (TU)/animal in female beagle dogs (N = 4)

| Treatment Group | $T_{max}$ | $C_{max}$ | $t_{1/2}$ | $AUC_{0\text{-}last}$ | $AUC_{INF}$ | $AUC_{0\text{-}last}$ (T)/ $AUC_{0\text{-}last}$ (TU) |
|---|---|---|---|---|---|---|
|  | hr | ng/mL | hr | hr * ng/mL | hr * ng/mL | % |
| *PK parameters of Testosterone in fasted study* | | | | | | |
| FD1 | 2.38 | 11.5 | 1.56 | 33.7 | 35.6 | 3.88 |
| FD2 | 2.50 | 18.4 | 0.752 | 48.3 | 50.7 | 2.33 |
| FD3 | 2.25 | 22.3 | 0.877 | 57.6 | 58.7 | 3.07 |
| FD4 | 2.50 | 16.8 | 0.951 | 50.8 | 53.4 | 2.74 |
| FD5 | 2.50 | 18.8 | 1.62 | 47.9 | 56.0 | 2.76 |
| FD6 | 1.75 | 4.13 | 0.728 | 7.89 | 11.5 | 2.90 |
| FD7 | 1.75 | 46.2 | 1.07 | 93.1 | 94.4 | 2.31 |
| Andriol ® | 1.63 | 4.12 | 0.938 | 8.06 | 10.4 | 4.00 |
| *PK parameters of Testosterone in fed study* | | | | | | |
| FD3 | 2.00 | 19.7 | 1.99 | 64.6 | 70.5 | 3.31 |
| FD7 | 1.50 | 21.0 | 1.29 | 53.6 | 54.5 | 2.41 |
| Andriol ® | 1.38 | 10.2 | 1.27 | 27.7 | 29.7 | 2.92 |

Example 4: Stability Study of Solid Oral Dosage Forms

A pilot stability study was conducted on soybean oil and olive oil SEDD prototypes loaded into tablets. The SEDDS had a composition as described in example 1, Table 1 for D1 and D2 respectively. One quarter of the oil relative to the D1 and D2 formulations (i.e. 260 mg) was loaded into corresponding quarterly sized core tablets to form 10 mg TU prototype tablets with a SEDDs system Olive oil:Mono-oleate 1:3 with Polysorbate 80:Polyoxyl 35 castor oil 1:1, 60% fat (formulation D1A) and Soybean Oil:Mono-oleate 1:1 with Polyoxyl 35 castor oil, 60% fat (formulation D2A). The tablets were put on stability at room temperature each in a 25 ml glass vial closed with PTFE insert in the screw-cap.

The formulations were analyzed for potency and related impurities by extraction of the tablets with methanol and analysis on an HPLC system consisting of a Kromasil C18, 250×4.6 mm 5 μm HPLC column kept at 30° C. and eluted with methanol as mobile phase and detection at 260 nm. Currently 6 months data are available for both formulations. The results are given in the table 13.

TABLE 13

Stability of formulations D1 and D2 containing 10 mg of TU/tablet

| Potency at 25° C./60% RH (mg/tablet) | start | 1 month | 3 months | 6 months |
|---|---|---|---|---|
| Formulation D1A | 11.0 | 8.9 | 9.4 | 8.8 |
| Formulation D2A | 10.0 | 10.4 | 10.3 | 11.0 |

Two (2) TU related impurities was observed after 6 month in the extract from formulation D1A each of approx. 5% whereas the impurities in the extract from formulation D2A were each 1% or less in abundance after 6 months storage.

Example 5: Solubilization of Testosterone Undecanoate (TU) in Formulations

The formulations FD2, FD3, and FD7 from Example 2 were compared with the commercial TU product Andriol® capsules in a solubilization experiment for their ability to release and solubilize TU in 900 ml aqueous medium with 2% SLS. The experiment was conducted in a paddle USP 2 dissolution apparatus at 37° C. with a paddle rotation speed of 100 RPM. Fractions taken at regular intervals were analyzed by HPLC using a column: Kinetex C18, 50×4.6 mm, 5 μm, column temp.: 40° C., mobile phase: 10% water in methanol, flow: 1.5 mL/min. at a wavelength 260 nm, run time: 4 min.

TABLE 13

Amount TU released and solubilized in % of nominal content at various time points

| | T = 0 Min | T = 20 Min | T = 40 Min | T = 60 Min | T = 80 Min | T = 120 min | T = 180 min | T = 240 min | T = 300 min |
|---|---|---|---|---|---|---|---|---|---|
| FD2 | 0 | 10.2 | 15.7 | 25.2 | 32.9 | 40.6 | 47.8 | 51.6 | 52.2 |
| FD3 | 0 | 28.1 | 29.9 | 35.6 | 38.7 | 40.6 | 42.6 | 44.6 | 43.4 |
| FD7 | 0 | 50.,4 | — | 56.6 | 56.5 | 56.2 | 56.0 | 55.6 | 56.2 |
| Andriol ® | 0 | 7.4 | 13.7 | 12.2 | 12.2 | 12.2 | 11.9 | 12.2 | 12.2 |

While the invention has been described with a certain degree of particularity, many changes may be made in the details of construction and the arrangement of components without departing from the spirit and scope of this disclosure. It is understood that the invention is not limited to the embodiments set forth herein for purposes of exemplification, but is limited only by the scope of the attached claims, including the full range of equivalency to which each element thereof is entitled.

I claim:

1. An oral pharmaceutical composition comprising a testosterone derivative having a log P of at least 5, wherein the testosterone derivative is selected from testosterone undecanoate, testosterone enathate, testosterone oleate, or testosterone palmitate, wherein the testosterone derivative is present in an amount from about 0.5% to about 20% by weight based on 100% total weight of the composition, and a vehicle, wherein the vehicle comprises (a) a fat component comprising a monoglyceride and a triglyceride of long chain fatty acids wherein the amount of monoglyceride and triglyceride of long chain fatty acids in the fat component is at least about 500 mg sufficient to achieve lymphatic absorption in a mammal, wherein the long chain fatty acids in the monoglycerides are selected from fatty acid chains having from 14 to 22 carbon atoms and the long chain fatty acids in the triglycerides are selected from fatty acid chains having from 14 to 22 carbon atoms, wherein the weight ratio of triglycerides to monoglycerides is in a range from about 2.8:1 to about 1:5, and (b) a hydrophilic surfactant, wherein the hydrophilic surfactant is selected from hydrogenated castor oil ethoxylates, polysorbates or any other hydrophilic surfactant with a Hydrophile-Lipophile Balance (HLB) value of 10 or higher, and any combination thereof, wherein the weight ratio (a):(b) is from about 10:1 to about 1:1 and wherein composition exhibits an AUC(0-inf)(fasted)/AUC (0-inf)(fed)) of at least about 0.8.

2. The composition of claim 1 wherein the fat component is present in an amount sufficient to enhance or promote intestinal lymphatic transport of the testosterone derivative upon oral administration in the fasted state as well as in the fed state, compared to a composition without the fat component.

3. The composition of claim 1 wherein the amount of fat component is from 500 mg to 1200 mg.

4. The composition of claim 1, wherein the weight ratio of (a):(b) ranges from about 4:1 to about 1:1.

5. The composition of claim 1, wherein the long chain fatty acids in the monoglycerides are selected from linoleic acid, oleic acid, palmitic acid, linolenic acid, or stearic acid.

6. The composition of claim 1 wherein the long chain fatty acids in the triglycerides are selected from linoleic acid, oleic acid, palmitic acid, linolenic acid, or stearic acid.

7. The composition of claim 1, wherein the fat component comprising a triglyceride of long chain fatty acids is selected from a naturally derived oil, such as soybean oil, olive oil, sesame oil, safflower oil, peanut oil, rapeseed oil, sunflower oil, coconut oil, corn oil, sunflower seed oil, cotton seed oil, palm oil, arachis oil, or any combination thereof.

8. The composition of claim 1, wherein the fat component is selected from olive oil, soybean oil, mixtures of olive oil and glycerol mono oleate, and, mixtures of soybean oil and glycerol mono oleate.

9. The composition of claim 1, wherein the composition is self-emulsifying.

10. The composition of claim 1, wherein the composition, upon dilution in purified water, forms droplets which a d50 of less than about 40 micrometers.

11. The composition of claim 1, wherein the testosterone derivative is in a solid core.

12. The composition of claim 11, wherein the vehicle is loaded into the solid core.

13. The composition of claim 12, wherein the testosterone derivative is dissolved in the vehicle and loaded into the solid core.

14. The composition claim 1, wherein the composition is a solid dosage form and said solid dosage form is a compressed or molded tablet having a hardness of from about 20 N to about 150 N.

15. The composition of claim 1 being selected from a liquid, a gel, a granula, a capsule or tablet.

16. The composition of claim 1 wherein the testosterone derivative is testosterone undecanoate in an amount of from about 10 mg to 200 mg.

17. The composition of claim 1 wherein the testosterone derivative is testosterone undecanoate and wherein at least 25% of the testosterone undecanoate is dissolved and solubilized from said composition within 180 minutes, as determined by USP XXIII Paddle Method II using 900 ml water containing 2% SLS at 37° C. as the dissolution media and 100 rpm as the stirring rate.

* * * * *